US00PP20013P2

(12) United States Plant Patent
Lindgren

(10) Patent No.: US PP20,013 P2
(45) Date of Patent: May 19, 2009

(54) ***PENSTEMON* PLANT NAMED 'DARK TOWERS'**

(50) Latin Name: *Penstemon hybrid*
Varietal Denomination: Dark Towers

(75) Inventor: Dale Tennis Lindgren, North Platte, NE (US)

(73) Assignee: Board of Regents of the University of Nebraska-Lincoln, Lincoln, NE (US)

( * ) Notice: Subject to any disclaimer, the term of this patent is extended or adjusted under 35 U.S.C. 154(b) by 0 days.

(21) Appl. No.: 12/001,347

(22) Filed: Dec. 10, 2007

(51) Int. Cl.
*A01H 5/00* (2006.01)

(52) U.S. Cl. ..... Plt./465
(58) Field of Classification Search ..... Plt./465
See application file for complete search history.

*Primary Examiner*—Kent L Bell
(74) *Attorney, Agent, or Firm*—Klarquist Sparkman, LLP

(57) ABSTRACT

A new and distinct *Penstemon* plant characterized by an upright, dense habit with very dark foliage, flowers of light purple shades, and excellent vigor.

1 Drawing Sheet

Botanical denomination: *Penstemon* hybrid.
Variety designation: 'Dark Towers'.
Parentage: *Penstemon digitalis,* 'Husker Red'×*Penstemon* 'Prairie Splendor' (*Penstemon cobaea*×*Penstemon triflorus*).

BACKGROUND OF THE INVENTION

The present invention relates to a new and distinct *Penstemon* and given the cultivar name of 'Dark Towers'. *Penstemon* is in the family *Scrophulariaceae.* The new cultivar originated as part of planned breeding program at the University of Nebraska to improve *Penstemon digitalis* 'Husker Red'. The seed parent was *Penstemon digitalis* 'Husker Red' (an unpatented plant) and the pollen parent was *Penstemon* 'Prairie Splendor' (*Penstemon cobaea*×*Penstemon triflorus*), an unpatented plant.

SUMMARY OF THE INVENTION

This new *Penstemon* is distinguished by:

1. an upright, dense habit with very dark foliage,
2. flowers of light purple shades,
3. and excellent vigor.

This new cultivar has been reproduced only by asexual propagation (cuttings and tissue culture). Each of the progeny exhibits identical characteristics to the original plant. Asexual propagation by tissue culture using standard micropropagation techniques with terminal shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

Plants of the new *Penstemon* differ from plants of the parental cultivars primarily in flower color.

BRIEF DESCRIPTION OF THE DRAWING

The photograph shows the flowers, foliage, and habit of a two-year-old *Penstemon* 'Dark Towers' in June in Canby, Oreg.

DETAILED PLANT DESCRIPTION

The following is a detailed description of the new *Penstemon* based on observations of two-year-old specimens grown in the ground in full sun in the trial fields in June in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zones 3 to 8.
- *Size.*—50 cm wide and 75 cm tall.
- *Form.*—basal rosette with upright flowering stems.
- *Vigor.*—Excellent.
- *Stems.*—Grows to 75 cm tall and 7 mm wide, glabrous, internodes 5 to 7.5 cm long, Greyed Purple 187B.
- *Roots.*—Fibrous network, Grey Brown 199D.

Leaf:
- *Type.*—Simple, sessile.
- *Shape.*—Oblong to oblanceolate.
- *Arrangement.*—Opposite.
- *Blade size.*—Grows to 16.5 cm long and 3.5 cm wide.
- *Margins.*—Serrate.
- *Apex.*—Acuminate.
- *Base.*—Clasping.
- *Venation.*—Pinnate.
- *Surface texture.*—Glabrous on both sides.
- *Color.*—Topside between Greyed Purple 187A and Brown 200A on new growth outside half of the leaf in full sun lightening to Green 139B where shaded with the main vein Greyed Purple 187B; bottom side—Greyed Purple 187A to Green 137B mostly on bottom half and Greyed Purple 187A on top half.

Inflorescence:
- *Type.*—Panicle.
- *Size.*—Grows to 16 cm long and 10 cm wide.
- *Number of blooms per panicle.*—50 to 75.
- *Peduncle.*—Grows to 17 cm long, 2 mm wide, glandular, Greyed Purple 187B.

*Pedicel.*—Grows to 5 mm long, glandular, Greyed Purple 187B.

Flower bud:

*Size.*—Grows to 24 mm long and 5 mm wide.

*Shape.*—Tubular ovoid, down facing.

*Surface.*—Glandular.

*Color.*—Basal ⅓ is Red Purple 71A, the rest is Purple 87C except on the underside where it is Green White 187A to Yellow Green 154D.

Flower:

*Type.*—Perfect.

*Shape.*—Tubular, bilabiate.

*Size.*—34 mm long and 20 mm wide.

*Corolla description.*—Overall size is 34 mm long and 20 mm wide, tubular bilabiate, glabrous inside and glandular outside; tube is 25 mm long overall and 10 mm wide, with the basal ⅓ constricted and 3 mm wide; lobes 5 in number, reflexed; 3 basal lobes and 2 upper lobes, each 5 mm long and 5 mm wide, entire, obtuse; main color outside Purple 76A with the constricted part of the lobe Purple 77A, main inside color Purple 76C lightening to 76D on lobes, base and bee tracks to basal 3 lobes Purple 77A.

*Calyx description.*—10 mm wide and 5 mm long, stellate campanulate, glandular on both surfaces, 5 reflexed lobes, each 5 mm long and 1.5 mm wide, entire, acuminate; color overall between Black 202A and Greyed Purple 187A.

*Pistil description.*—1 in number, 25 mm long and 2 mm wide, ovary 4.5 mm long and 2 mm wide, between Black 202A and Greyed Purple 187A; style 20 mm long, filiform, Purple 76B, stigma 0.5 mm, White 155A.

*Stamen description.*—4 in number, 22 mm long, filaments 20 mm long, Purple 76A, anthers 2 mm long and 2 mm wide, Black 202A; pollen White 155D.

*Bloom period.*—June to August in Canby, Oreg.

*Lastingness of bloom.*—Each flower lasts about a week.

*Fragrance.*—None.

Fruit: a capsule, 10 mm long and 6 mm wide, glabrous, Brown 200A.

Seed: sterile, none produced.

Pest and diseases: Snails and slugs may be a problem on young plants. This variety has no known resistances.

I claim:

1. A new and distinct *Penstemon* plant as herein illustrated and described.

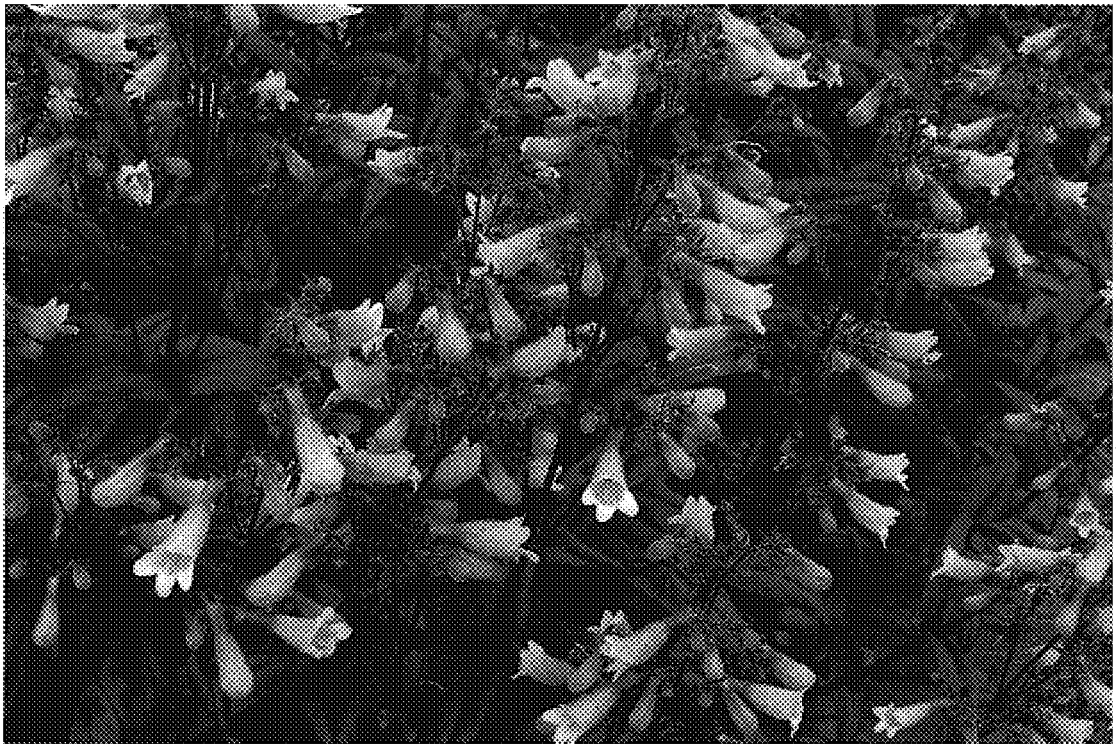

* * * * *